United States Patent [19]

Born et al.

[11] Patent Number: 5,240,693

[45] Date of Patent: Aug. 31, 1993

[54] IMAGE ENHANCEMENT BY COADMINISTRATION OF BIOMODULATORS AND STRUCTURALLY MODIFIED IMAGING AGENTS

[75] Inventors: Jerry L. Born; Dennis Eshima; Frank O. Kroh; Paul L. Mann, all of Albuquerque, N. Mex.

[73] Assignee: University of New Mexico, Albuquerque, N. Mex.

[21] Appl. No.: 694,157

[22] Filed: May 1, 1991

[51] Int. Cl.$^5$ .................. A61K 49/00; A61B 6/00
[52] U.S. Cl. .................................. 424/4; 514/23; 424/1.1; 424/2; 424/9; 128/653.1; 128/653.2; 128/653.4; 128/653.5; 548/453
[58] Field of Search .............. 514/53; 424/1.1, 4, 424/2, 9; 128/653.1, 653.2, 653.4, 653.5; 548/453

[56] References Cited

U.S. PATENT DOCUMENTS

| | | | |
|---|---|---|---|
| 4,352,751 | 10/1982 | Wieder et al. | 424/7.1 |
| 4,432,907 | 2/1984 | Wieder et al. | 424/7.1 |
| 4,647,447 | 3/1987 | Gries et al. | 424/2 |
| 4,719,098 | 1/1988 | Weinmann et al. | 128/653.4 |
| 4,728,575 | 3/1988 | Gamble et al. | 128/653.4 |
| 4,859,450 | 8/1989 | Khaw et al. | 128/653.4 |
| 4,880,007 | 11/1989 | Sadler et al. | 128/654 |
| 4,925,648 | 5/1990 | Hansen et al. | 424/1.1 |
| 4,926,869 | 5/1990 | Rubin et al. | 424/1.1 |
| 4,933,441 | 6/1990 | Gibby | 424/1.1 |
| 4,957,939 | 9/1990 | Gries et al. | 424/1.1 |
| 4,963,344 | 10/1990 | Gries et al. | 424/9 |
| 4,972,837 | 11/1990 | Engelstad et al. | 128/64 |
| 5,019,368 | 5/1991 | Epstein et al. | 424/1.1 |
| 5,021,236 | 6/1991 | Gries et al. | 424/9 |
| 5,057,301 | 10/1991 | Wilbur et al. | 424/1.1 |
| 5,077,037 | 12/1991 | Wallace | 128/654 |

OTHER PUBLICATIONS

Mann et al., "Cell Surface Oligosaccharide Modulation during Differentiation: IV. Normal and Transformed Cell Growth Control," *Mechanisms of Ageing and Development*, 44 (1988), pp. 17-33.

*Primary Examiner*—Ronald W. Griffin
*Attorney, Agent, or Firm*—Millen, White, Zelano & Branigan

[57] ABSTRACT

Biomodulators can be administered together with an agent such as a drug or an imaging agent (specific or non-specific) structurally modified to take advantage of perturbations of cell oligosaccharide displays caused by biomodulators, to enhance images of a host, e.g., NMR-, X-ray- or radioimages, preferably by increasing aberrant tissue signal intensity. Biomodulators condition tissue to enhance or otherwise modify up-take of the drug or structurally modified imaging agent.

25 Claims, 2 Drawing Sheets

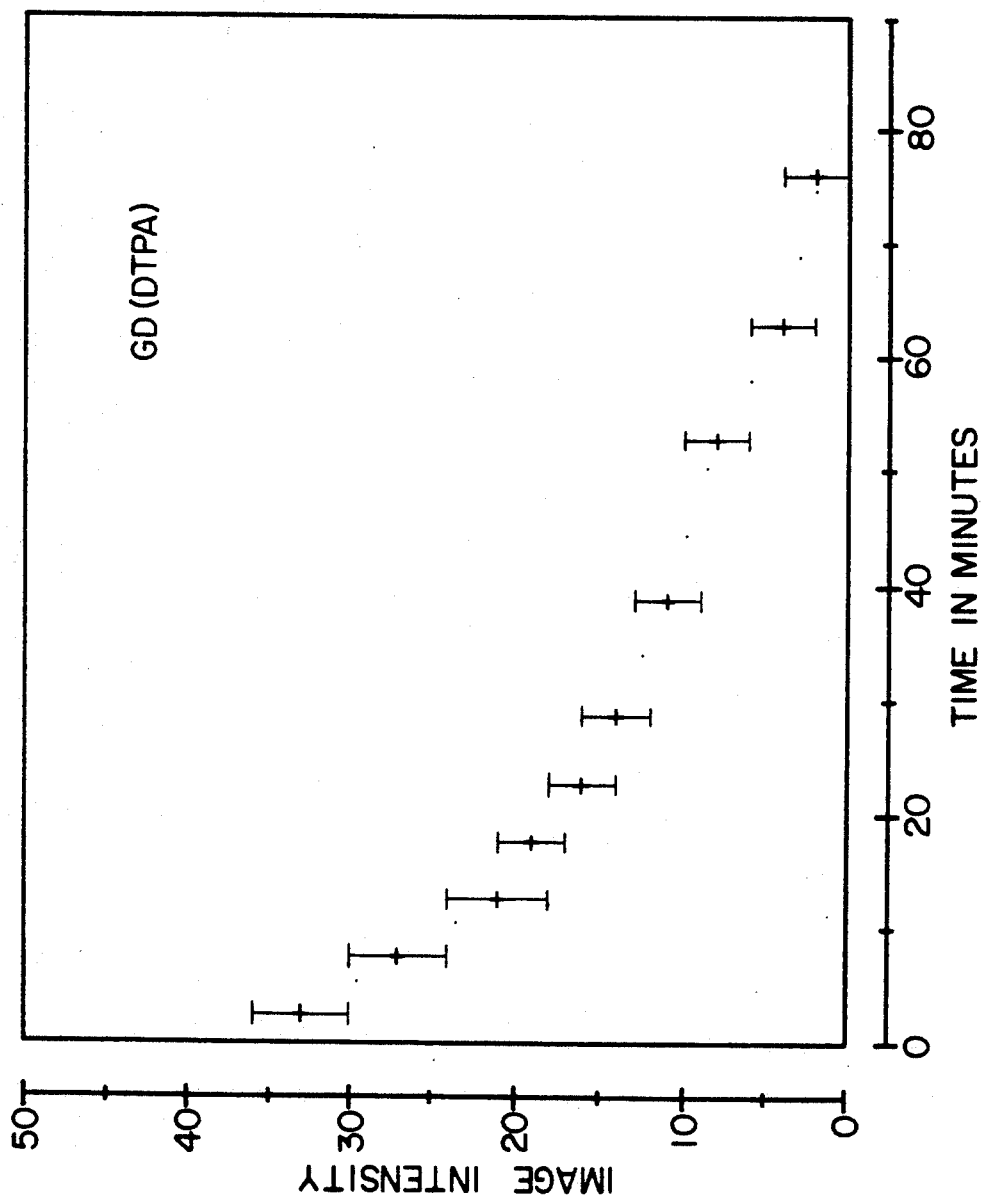

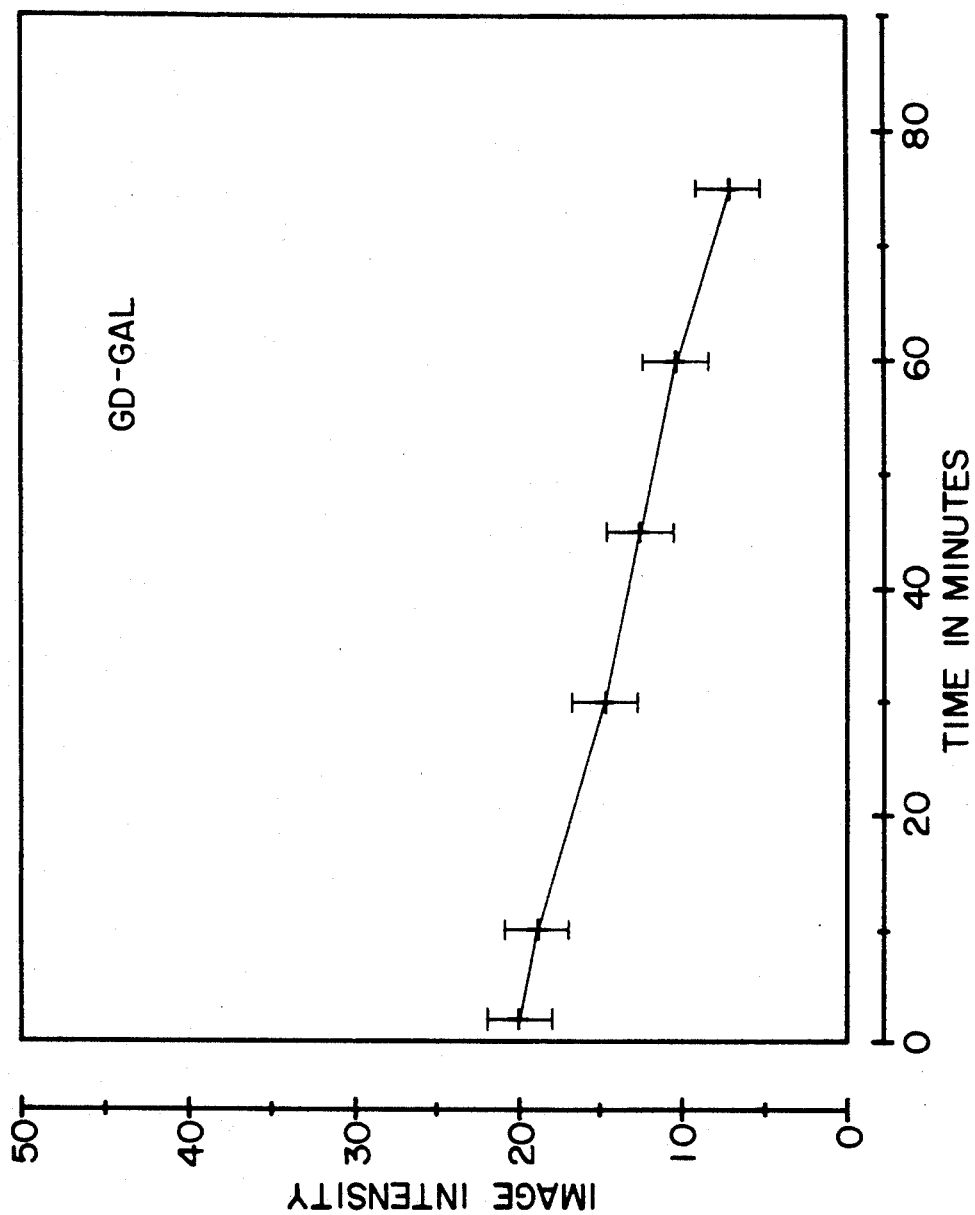

IMAGE ENHANCEMENT BY COADMINISTRATION OF BIOMODULATORS AND STRUCTURALLY MODIFIED IMAGING AGENTS

This application is related to Ser. No. 07/694,321, filed May 1, 1991, now abandoned, Ser. No. 07/694,325, filed May 1, 1991 and Ser. No. 07/694,151, filed May 1, 1991, all entirely incorporated by reference herein.

BACKGROUND OF THE INVENTION

One of the most difficult problems in in vivo imaging of living organisms is how to distinguish between normal and aberrant tissue. Many approaches to this problem have been developed, including inter alia, X-ray imaging (including CAT-scanning), radionuclide imaging, fluoroscopy, ultrasonic imaging and nuclear magnetic resonance (NMR) imaging (MRI), with and without the administration of imaging agents, e.g., contrast media. The imaging agent may comprise materials which are themselves opaque to the detection signal and simply increase the contrast between organs or tissues containing it and organs or tissues which do not, e.g., as with X-ray agents. Alternatively, the agent can be one which has a local effect on the endogenous moiety active to the modality, as in the effect of NMR contrast agents on protons in vivo. For example, such agents may comprise materials which are selectively biodistributed due to pharmacokinetics or affinity for a certain compound, cell type, tissue, organ etc. In the latter case, the agent will highlight those areas containing the matter for which the agent has affinity; in the former, it will highlight the areas where it is selectively transported. Many such imaging agents are well known in the relevant arts, as are methods of use thereof.

Each of the known agents and methods suffers from a variety of deficiencies related to tolerability of the imaging agent, invasive nature of the active radiation and efficiency and accuracy of the diagnosis enabled by the resulting image.

Under many circumstances each modality provides very detailed information by imaging of various tissues. However, each suffers from a limitation based upon the lack of distinction between normal and aberrant tissue which has the same imaging modality signature. Although several approaches have been taken toward increasing the specificity of contrast agents (often in combination with targeting agents, e.g., antibodies), and thus expanding the applicability of a given modality, these are limited in that they rely on administration of materials, e.g., antibodies, whose in vivo specificity is essentially unalterable. The known contrast agents, such as, e.g., gadolinium-DTPA for MRI, are not universally specific for all abnormal vs. normal tissue. What is needed are contrast agents for each modality which are specific for a wider variety of aberrant tissue versus its normal tissue counterpart, to provide overall applicability as universally as possible, and which can correspondingly be used to locate and diagnose aberrant tissues in a large proportion of the body of a living organism.

SUMMARY OF THE INVENTION

The present invention provides a method of enhancing the image of tissue obtainable by a particular imaging modality comprising administering a biomodulator and an imaging agent for said modality, said biomodulator and said agent and the amounts thereof being effective for enhancement or other modification of the imaging of said tissue, and said agent comprising:

a first portion per se effective to affect the image achievable by said modality; and a second, mono- or oligosaccharide portion effective to interact with cellular oligosaccharide displays.

In another aspect, this invention provides a method of delivering a drug to a particular site in a body of a host containing abnormal tissue comprising administering a biomodulator and said drug, the amounts of said biomodulator and said drug being effective to selectively concentrate said drug at said site of abnormal tissue, and said drug comprising:

a first portion per se effective to treat said abnormal tissue; and a second, mono- or oligosaccharide portion effective to interact with cellular oligosaccharide displays.

The invention also provides a pharmaceutical kit comprising a container comprising a biomodulator and a separate container comprising a therapeutically active agent or an imaging agent for an imaging modality comprising:

a first portion per se effective to affect the image achievable by said modality; and a second, mono- or oligosaccharide portion effective to interact with cellular oligosaccharide displays.

In a preferred aspect, the first portion of the imaging agent is non-tissue-specific or tissue-specific, the tissue is abnormal, such as that of a tumor, and the second portion of the imaging agent is a mono- or disaccharide.

Biomodulators

Biomodulators are natural products or synthetic compounds, e.g., analogs of a natural product which perturb the normal cellular differentiative and proliferative activity of eucaryotic, particularly mammalian, particularly human, cells. This biomodulatory activity is non-cell-lineage specific, affecting differentiation and proliferation in substantially all species and substantially all cell types. The activity of these compounds is considered to be at a primitive level of cellular control, common to all cells, and the compounds are therefore non-specific in their effect and production by cells. Thus, biomodulators as defined herein are distinct from so-called "biological response modifiers," such as, e.g., interleukins, interferons and other "kines," which have highly specific activities, and which are specific natural products of specific stimuli produced by specific highly specialized cell types.

Without wishing to be bound by theory, it is believed that the activity of biomodulators is based upon a generic, cell-surface oligosaccharide dependent model for "primitive" phenotypic expressions of differentiation. This theory is discussed in P. L. Mann, Intl. Rev. Cytol. 12, 67-95 (1988), which is incorporated herein by reference.

Preferred "biomodulators" include compounds selected from
(a) a compound of formula (I)

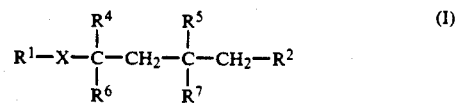

wherein $R^1$ is an optionally substituted aromatic, cycloaliphatic or heterocyclic ring system,
$R^2$ is —CH$_2$OH, —CHO, —COOR$^3$, —COSR$^3$, —CONR$^8$R$^9$ or the corresponding lactone

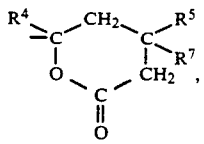

wherein
$R^3$ is H or C$_{1-10}$-alkyl,
$R^4$ and $R^5$ are each independently H or C$_{1-6}$-alkyl,
$R^6$ and $R^7$ are each independently OR, NHR or SR wherein R is H or C$_{1-4}$-alkanoyl,
$R^8$ and $R^9$ are each independently H or C$_{1-10}$-alkyl, and
X is C$_{2-3}$-alkylene, C$_{2-3}$-alkenylene, C$_{2-3}$-alkynylene, a cyclopropylene group, —OCH$_2$— or —SCH$_2$—;
(b) a compound of formula (II) (swainsonine)

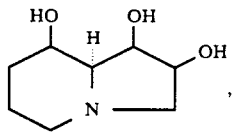

or an indolizidine alkaloid having an electronically similar 1,3-diol structure;
(c) cellular activator and differentiator (CAD); and
(d) pokeweed mitogen; and having the biological activity of a biomodulator as described herein.

A first category of compounds useful in the methods of the present invention comprises compounds of formula (I) as described above. Particularly preferred compounds within the scope of formula (I) are those which have a steric configuration at the 3,5-carbon atoms of the heptanoic or octanoic acid based diol chain which is substantially electronically similar to that of the 3S,5R, 3S,5S or 3R,5R configurations of colletruncoic acid. By "substantially electronically similar" is meant that in the energy minimized form, the interhydroxyl distance between the relevant hydroxyl groups is between 4.2–4.4 Å, preferably about 4.3 Å. The electronic similarity of the compounds can be determined, e.g., by performing routine energy minimization calculations, e.g., utilizing conventional calculations, such as those performed by the Chemdraft Computational Package, program MM-2, (C-Graph Software, Inc., Austin, Tex. 78763). In general, compounds which have a configuration 3R,5S (when X is an alkylene group, i.e., is saturated) or equivalently 3S,5R (when X is an alkenylene or alkynylene group, i.e., is unsaturated) will correspond to this most preferred structure. 3R,5R- and 3S,5S- configurations are also preferred.

The radical $R^1$ has a variable effect. In general, the $R^1$ radical is substantially hydrophobic with well defined pockets of electronegativity. Suitable $R^1$ ring groups have 1–4 or more fused and/or covalently bonded rings, optionally substituted by substituents which render this portion of the molecule electronegative (e.g., OH, halo, NO$_2$, NH$_2$, COOH, etc.). The compounds of formula I can possess $R^1$ ring groups having a hydrophobicity and/or electronegativity on the order of those of one or more of the following suitable $R^1$ rings, including C$_{6-25}$ mono-, bi-, tri- or polynucleararyl, -aryloxy, -cycloalkyl, -cycloalkenyl, -cycloalkadienyl, etc., as well as heterocyclic rings containing or sharing one or more, e.g., 2 or 3, O, S or N atoms. Where fused systems containing 1–4 or more individual rings are involved, each ring generally contains 4–7 atoms, 1–3, preferably, 1–2, of which are O, N or S atoms, the remainder being C atoms, these generally having 1–4 hetero atoms in total. Thus, heteroaryl and hydroheteroaryl groups are suitable. Examples of suitable $R^1$ groups include benzyl, benzyloxy, phenyl, phenyloxy, naphthyl, naphthyloxy, tetrahydronaphthyl, hexahydronaphthyl, octahydronaphthyl, imidazolyl, pyrimidyl, pyrazolyl, indenyl, quinolinyl, pyrrolyl, indolyl, indolizinyl, etc.

In addition, particularly preferred compounds of formula (I) are those in which n is 1, $R^2$ is COOR$^3$ or the corresponding lactone, $R^4$ and $R^5$ are each H, $R^6$ and $R^7$ are each OH, and X contains a cis or trans double bond.

One subtype of these compounds useful in the methods of the present invention are relatively small (for example, molecular weight less than 1,000 daltons) naturally occurring compounds (in isolated form) having the structure of formula I and the required electronic structure at the 3,5-carbon atoms. For example, the appropriate enantiomer of colletruncoic acid as defined above,

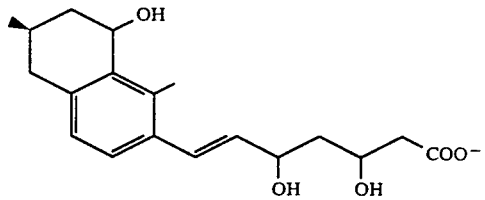

a natural compound isolated from *Colletotrichum truncatum*, has a structure encompassed by the structural formula described above and has been shown to have biomodulator activity. Colletruncoic acid can be isolated according to the method outlined in Stoessl, A., and Stothers, J. B., Z. Naturforsh. 41c, 677–680 (1986), except as modified in that Stoessl et al. described the natural product as being a racemic methylester, which is incorrect; the correct compound is a free acid of one enantiomer with the noted stereochemistry.

Another subtype of these compounds are synthetic compounds of formula I having the required electronic structure at the 3,5-carbon atoms, as described above. All compounds of formula I can be made, in general, from readily available and/or preparable starting materials according to routine chemical syntheses, for example, according to methods outlined in U.S. Pat. Nos. 4,755,606, 4,613,610, 4,255,444, 4,248,889, 4,761,419, 4,751,235, 4,198,425, 4,137,322, 3,983,140, 4,588,715, 4,710,513, 4,739,073, 4,681,893; WO 84/92903; WO 87/02662; WO 88/01997; and WO 86/03488. For joining $R^1$-X-C (wherein C is the rest of the molecule) when X is CH$_2$CH$_2$, see *Tetrahedron* 1986, 42, 4909–4951. For joining $R^1$-X-C when X is —CH═CH—, a selenoxide or sulfoxide coupling and elimination strategy can be employed (see *J. Org. Chem.*, 1986, 51, 648–657) or, alternatively, Wittig methodology (see *J. Org. Chem.*, 1984, 49, 3994–4003.). When X is —C≡C—, the acetylide $R^1$—C≡C can be added to an appropriate aldehyde or ketone. When X is —OCH₂— or —SCH₂— then R¹O− or R¹S− will be condensed with an appropriate electrophile; see *Tetrahedron Lett.,* 1988, 29, 2563-2566. Similarly, the R¹ moieties bearing substituted groups can be synthesized either before or after linkage to the remainder of the molecule.

A second general category of compounds having a related structure and having biomodulator activity is constituted by other small, naturally occurring compounds such as, e.g., swainsonine,

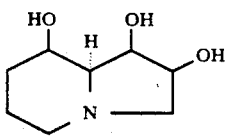

which is a low molecular weight indolizidine alkaloid extracted from *Swainsona sp.* as well as from a number of other natural sources, and has hydroxy groups on its ring which have an almost identical electronic structure to the hydroxy groups on the heptanoate chain as described above. (Swainsonine is known to have anticancer effects possibly mediated through its inhibition of α-mannosidase II; thus, this effect is not suggestive of its biomodulator role or its range of activities in the other utilities described above. See, e.g., Newton, S. A., et al., J. Natl. Cancer Inst. 81, 1024-1033 (1989); Dennis, J. W. et al., Cancer Res. 50, 1867-1872 (1990).) Swainsonine is commercially available, e.g., from Boerringer-Mannheim, or can be isolated according to the method outlined in Hino, M, et al., J. Antibiotics 38, 926-935 (1985). Other members of this category are, e.g., other indolizidine alkaloid compounds retaining the electronic structure of the important "1,3-diol array" of swainsonine, such as swainsonine substituted in the ortho and meta positions on the 6-membered ring by hydroxy groups (castanospermine) and other natural products having an electronically similar 1,3 diol array. Still other suitable alkaloids are related compounds having two 6-membered rings or two 5-membered rings.

In addition to the known natural low molecular weight compounds swainsonine and colletruncoic acid, a third major type of biomodulator is a new compound provided by the present invention having properties similar to the compounds of Formula I. This compound, cellular activator and differentiator or CAD, is isolated from *Penicillium restrictum,* has a molecular weight of about 500, and is believed, without wishing to be bound by theory, to have a similar structure to colletruncoic acid. It can be isolated according to the method outlined in.

A fourth category of compounds useful in the methods of the present invention are high molecular weight compounds having biomodulator activity, such as pokeweed mitogen (PWM), which is a well known mixture of five isomitogenic glycopeptides extracted from *Phytolacca americana,* and which is known for its ability to stimulate cellular proliferation. Although its structural relationship to the above described compounds is uncertain, PWM is thought to interact with cells in a similar way and has the same spectrum of effects for the various utilities disclosed herein. Pokeweed mitogen can be isolated according to well-known methods, e.g., according to the method outlined in Riesfeld, R. A., et al., Proc. Natl. Acad. Sci. (U.S.) 58. 2020-2027 (1967). It is noted that the differentiative and proliferative activities of PWM can be separated, i.e., by separating the isotypes, e.g., according to the method of Waxdal, M.J., Biochem. 13, 3671 (1974). The differentiative substance is preferred.

Preferred compounds include 3S,5R-colletruncoic acid and the compound obtained by switching the heptanoate chain of 3S,5R-colletruncoic acid with the adjacent methyl group on the ring.

Biomodulator Activities

Cellular functions can be broadly divisible into two general categories: proliferation (reproduction) and differentiation (specialization of function). According to present theory, the proliferative function is continuously present in the normal cell, and is dominated in the mature cell by the differentiative function, which . thus acts as an integrative force to regulate both differentiative and proliferative functions in the mature cell. A failure in the biochemical mechanisms upon which the cell is dependent for control of cell differentiative and proliferative functions thus has important implications, as disruption of normal differentiative and proliferative controls may result in both abnormal cellular function and abnormal cellular growth regulation. Thus, improperly enhanced cellular proliferation, particularly when coupled to impaired cellular differentiation may be a basis for neoplasia. Similarly, the well-known phenomenon of cellular senescence couples a failure of proliferation of terminally differentiated cells after a defined number of cellular generations.

Without wishing to be bound by theory, biomodulators exert their effects at the most fundamental level by influencing cellular differentiation behavior, particularly abnormalities therein. They, for instance, can induce differentiation by modulating expression of the cellular differentiative phenotype; inter alia, the biomodulators induce expression of unexpressed genes to significantly diversify cellular function, or to significantly increase existing cellular function. The biomodulators are believed to induce proliferation in senescent cells by biomodulating expression of the cellular proliferative phenotype by similar mechanisms. Overall, the biomodulators counteract aberrant proliferative or differentiative cellular function by stimulating intracellular biochemical controls to normalize cellular behavior. It is this ability of biomodulators to normalize abnormal cellular function, both differentiative and proliferative (usually indirectly by normalizing aberrant differentiative activity underlying the aberrant proliferation, but also directly, e.g., in the case of senescent cells), across a wide spectrum of cell types, which primarily underlies their usefulness.

The biomodulators effect their results in very low concentrations and are generally characterized by a relatively low (less than 1,000 daltons) molecular weight, higher weights, however, also being involved in some cases. The compounds are non-toxic in the amounts employed in the methods of the present invention. It is theorized that these compounds simulate or involve mechanisms controlling cellular differentiative behavior and/or integration of cell proliferation and differentiation activity on a primitive level, thus accounting for their influence on a broad range of biological effects.

As mentioned, one of the effects which biomodulators have been demonstrated to possess is their ability to normalize cellular function in cells which have become aberrant, e.g., tumor cells or senescent cells. In particular, from a mechanistic perspective, it has been shown that administration of biomodulators affects the conformational arrangements of simple cell-surface oligosaccharide structures in aberrant cells (Mann, P. L., et al., Mech. Ageing Devel. 44, 17–33 (1988)). This has been shown, for example, by determination of binding-class affinities and capacities for specific lectin/oligosaccharide combinations, with and without biomodulator influence. Scatchard analysis and the calculation of Gibb's Free Energy ($\Delta G$) were used for comparison purposes, as disclosed therein. The $\Delta G$ values obtained were found to be predictors of phenotypic changes and the efficacy of the biomodulators.

Characterization of the nature of these effects on the conformation of the cell-surface oligosaccharide displays was performed, inter alia, by NMR imaging on cells in culture, both aberrant and normal. It was found that cells which are about to undergo senescence, and thus are failing in their proliferative function, showed a significant narrowing in proton linewidth measurements of cell surface water, which was correlated with a "down-regulation" of the $\Delta G$ value of the cell surface oligosaccharide display. Treatment of the cells with biomodulators prevented the "down-regulation" and NMR proton linewidth changes, as well as the subsequent development of the senescent phenotype. On the other hand, neoplastic cells have cell surface oligosaccharide displays which are "in-between" those of normal and senescent cells, both in terms of $\Delta G$ values and the proton linewidths. Treatment of these cells with biomodulators "up-regulates" the oligosaccharide conformations, increases linewidth values, increases the ability of these cells to be recognized by cytotoxic lymphocytes (the normal phenotype) and decreases their generation times *in vitro*.

The above experiments are among those which demonstrate the effect of biomodulators on cell-surface oligosaccharide displays *in vitro*. Without wishing to be bound by theory, it is this association between the oligosaccharide displays of the aberrant cells and the biomodulators which underlies this invention, e.g., in view of the ability of biomodulators to modify, i.e., "normalize" aberrant tissue oligosaccharide displays. This modification of such displays thus mediates an altered biodistribution of an agent contacting tissue undergoing such a biomodulator modification, such as a drug or an imaging agent, especially when the latter is structurally modified by the presence of a mono- or oligosaccharide moiety, preferably a amino sugar. Assays for determining whether a new candidate structure is a biomodulator and/or for determining the activity profile of a biomodulator are given in detail in.

The biomodulators typically will selectively accumulate in areas of the body containing abnormal tissue. This occurs because of the ability of biomodulators to normalize aberrantly differentiating cells. Thus, the biomodulators will concentrate in and around such cells on which they are active, whereby they will have effect on such environments and not others. In some cases, a biomodulator may concentrate in normal tissue. In such event, which particular tissue is the target of a particular biomodulator will be routinely determinable by preliminary experiments involving administration of the biomodulator followed by conventional body scans by an imaging modality sensitive to the presence of a biomodulator, e.g., MRI as discussed in related application.

Because of the ability of biomodulators to selectively concentrate in abnormal or other tissue, they can be used as "targeting molecules," by preconditioning such tissue in a fashion such that an agent (therapeutic or diagnostic) interacting with such tissue will do so in a way different from that with tissue not pretreated with a biomodulator. Such agents are preferably structurally modified to possess an oligosaccharide component by which the agent's ability to take advantage of the effect of the biomodulator is enhanced. Thus, as indicated in the examples herein, when GdDTPA$^{2-}$, for example, is modified with one or more galactosamine residues, it interacts with biomodulator-treated tissue over time in a fashion (linear decay) significantly different from how it interacts with the same tissue not treated with a biomodulator (logarithmic decay), as measured by NMR imaging $T_1$ determinations. For MRI, the underlying physical phenomenon being measured can be any of the known parameters including $T_1$, $T_2$, proton density, chemical shift, etc.

Suitable oligosaccharides which can be used to modify imaging agents are mono-, di-, tri-, and tetraoligosaccharides and higher (e.g., up to 20 units) and combinations thereof. Suitable non-limiting examples include: trioses, tetroses, pentoses, hexoses, heptoses and octoses, including aldoses and ketoses of each; homo- and heteropolymers of each, up to 20 units, derivatives thereof, e.g., sugar alcohols, O-acyl derivatives, O-methyl derivatives, sugar acids, phosphoric acid esters, deoxy sugars, amino sugars, and amido sugars, including muramic and neuraminic acid. In particular, oligosaccharides which are found on cell surfaces, or oligosaccharides having related structures, are preferred. The naturally occurring stereoisomers are preferred. Monosaccharides such as galactose, glucose, mannose, fructose, N-acetyl neuraminic acid, N-acetyl muramic acid, glucuronic acid, glucosamine and galactosamine are preferred. Disaccharides such as lactose, maltose, sucrose, dimannose and digalactose, and Lactosamine, particularly when linked by naturally-occurring linkages, are also preferred. Galactosamine is especially preferred. Suitable imaging agents include all conventional imaging agents for the various imaging modalities. In particular, for MRI, imaging agents include chelates of paramagnetic ions, wherein the ligands include, e.g., DTPA (diethylenetriamine pentaacetic acid); DOTA (1,4,7,10-tetraazacyclododecane-1,4,7,10-tetraacetic acid); MAG3 (mercaptoacetylglycylglycylglycine), derivatives of MAG3 having additional CH$_2$-groups in the C-terminal end (HS—(CH$_2$—CO—NH)$_3$—(CH$_2$)$_n$ —COON, Wherein n=1-10). The mono- or oligosaccharides can be terminal or central on the ligands. For X-ray, the conventional iodinated benzenes can be used. In addition, any conventional imaging agent for any conventional imaging modality can be similarly glycosylated. Modified imaging agents can be routinely prepared, e.g., by employing in the standard chemical synthesis of a given conventional agent, instead of the usual starting materials, one or more of the latter containing the desired oligosaccharide moiety. Bonding of the latter to the suitable conventional starting material can be performed in any of several conventional ways involving standard linking of oligosaccharide residues to chemical agents via ester, ether, amide, etc., bonds, as discussed, e.g., in Inouye et al., J.Am. Chem. Soc. 78 4722–4724 (1956). Also, Sherry et al., Inorg. Chem. 28 620–622 (1989). For example, galactosamine-DTPA-Gd was prepared by Gd(gal$_2$-DTPA), prepared by the addition of anhydride of DTPA to aqueous galactosamine, followed by the addition of GdCl$_3$ according to the following procedure.

Syntheses and Characterizations

The agents consist of three or four components: the metal cation, the amino sugar, the ligand, and optionally an alkyl chain connecting the amino sugar to the ligand. After selecting the three or four specific components, assembly is most practically in the same order. First, the amino sugar (with or without an aminoalkyl group on the nitrogen of the amino sugar) is attached to the ligand (one or two amino sugars per ligand), then the structure and purity of the sugar-substituted ligand is determined by $^{13}$C NMR spectroscopy, and finally the metal ion is bound by the sugar-substituted ligand.

Step 1. For the DTPA-based ligands, the amino sugar is dissolved in chilled water, and the solid dianhydride of DTPA is added in small portions, with monitoring of pH, and sufficient NaOH is added to keep the pH above 8. As an example, the synthesis of Gd(2-gal)$_2$DT3A, Gd(2-glu)$_2$DT3A, Gd(2-man)$_2$DT3A are given. One gram of the appropriate hexosamine hydrochloride (4.64 mmoles, available from Sigma Chemical Co.) is dissolved in 20 mL of water, chilled to 0°, and sufficient 6 M NaOH is added to bring the pH to 9. Solid DTPA cyclic anhydride (caDPTA, available from Sigma Chemical Co., 0.737 grams, 2.06 mmoles, ca. 2.25 moles of amino sugar per mole of caDTPA) is slowly added, while continually monitoring pH. Aqueous 6 M NaOH is added as needed to keep pH above 8.

The procedure for the monoamidation of DOTA by organic amines has been described by Sherry et al., (Inorg. Chem. 28, 620–622 (1989)).

Step 2. A portion of the production of Step 1 is placed in an NMR tube, and a small amount of D$_2$O and 1,4-dioxane are added to provide a field-frequency lock and a chemical shift reference. The $^{13}$C NMR spectrum is acquired, and the dioxane peak is assigned a chemical shift of 67.86 ppm. The table gives the chemical shifts for the sugar moieties attached to any ligand based upon DTPA or DOTA:

|     | α0Gal | β-Gal | α-Glu | β-Glu | α-Man | β-Man |
| --- | --- | --- | --- | --- | --- | --- |
| C-1 | 92.30 | 96.63 | 92.14 | 96.18 | 94.23 | 94.43 |
| C-2 | 51.74 | 54.85 | 55.56 | 57.90 | 55.51 | 56.36 |
| C-3 | 68.78 | 72.24 | 71.76 | 74.88 | 70.20 | 73.88 |
| C-4 | 70.03 | 69.32 | 71.40 | 71.32 | 68.04 | 68.22 |
| C-5 | 71.91 | 76.51 | 72.92 | 77.19 | 73.64 | 77.88 |
| C-6 | 62.60 | 62.39 | 62.01 | 62.18 | 62.22 | 62.16 |

The presence or absence of unreacted amino sugar is determined by observing the C-1 region of the spectrum. Residual galactosamine.HCl has chemical shifts of 90.70 ppm (α) and 94.58 ppm (β); glucosamine.HCl resonates at 90.56 ppm (α) and 94.24 ppm (β); and mannosamine.HCl has peaks at 91.79 ppm (α) and 92.41 ppm (β).

The number of amino sugar groups on each DTPA ligand is determined by observing the carboxylate region of the $^{13}$C spectrum. FIG. 1 shows the $^{13}$C chemical shifts of the carboxylate carbons of model compounds (in which a 2-hydroxyethyl group replaces the sugar), as a function of pH. Similar chemical shifts are observed for all of the sugar derivatives. The carboxylate region of the spectrum is most indicative of the state of the DT3A or DT4A part of the molecule, because no sugar peaks are found here.

If further purification is necessary, the anion-exchange method reported by Sherry et al. (Magn. Reson. Med. 8, 180–190 (1988)) is employed.

Step 3. An aqueous solution of the metal is added to the aqueous ligand solution, such that a slight excess of the ligand remains. The gadolinium and dysprosium solutions are prepared by dissolving the chlorides MCl$_3$ in water, or the oxides M$_2$O$_3$ in strong organic or mineral acids, or by other established methods. For example, for the 2.06 mmoles of (2-gal)$_2$DT3A, (2-glu)$_2$DT3A, and (2-man)$_2$DT3A which were prepared in Step 1 and characterized in Step 2, a gadolinium chloride solution is prepared by dissolving 0.689 g of gadolinium trichloride hexahydrate (1.85 mmoles) in 10 mL of distilled water. Then, the GdCl$_3$ solution is added to the solution of the substituted DTPA ligand, and stirred for 15 min., to yield a solution of Gd(2-gal)$_2$DT3A, Gd(2-glu)$_2$DT3A, Gd(2-man)$_2$DT3A, which is diluted to the desired concentration, or lyophilized to a higher concentration. The aqueous $^{99m}$Tc solutions are prepared by the reduction of the pertechnetate ion in an excess of a reducing agent such as stannous ion or dithionite. Mixing the metal solution with the ligand solution, with stirring at room temperature, for 15 min., produces the claimed complex.

For each agent, the exact nature of the bond between the imaging agent (ligand) and the oligosaccharide-specific portion of the molecule is not critical, so long as the imaging-effective portion of the molecule is not inactivated, and the oligosaccharide-specific portion of the molecule is capable of interacting with the cell-surface of the biomodulator-stimulated aberrant cells when bound to the imaging agent, as in essentially all cases will be true.

Selection of a given mono- or oligosaccharide for use with a given biomodulator/tissue/imaging agent combination can be performed routinely, with a few orientation experiments. For example, essentially any mono- or oligosaccharide as described above will produce, for a given agent, a different biodistribution thereof vis-a-vis biomodulator-influenced tissue as compared with the biodistribution of the agent (with or without mono- or oligosaccharide modification) against non-biomodulator-influenced tissue. Thus, this invention, by modifying the agent's distributional characteristics, will compensate for deficiencies of the agent, such as side effects, imaging problems, therapeutic effect (in the related aspect of this invention) discussed herein. An optimal oligosaccharide/agent/tissue combination can thus be chosen simply by comparing the beneficial effects achieved with candidate combinations.

Preferred biomodulator-induced effects will be those where the concentration of the oligosaccharide-modified agent is increased, thereby enhancing image contrast. However, any difference in image effect induced by the biomodulator will provide diagnostically valuable information since two "views" of the subject tissue will thereby be made available. Moreover, the biomodulators of this invention, as shown in the examples, will also affect the retention/clearance rates of the agent, thereby providing variability in timing of, e.g., a sequence of images and in staging the state of the subject tissue.

Employment of chemical entities other than oligosaccharides in place of the latter to modify the active agents of this invention is also an equivalent aspect of this invention where the chemical entity serves the function of binding to (interacting with) oligosaccharide displays.

The oligosaccharides can be bonded to any agents active for various imaging modalities, such as, for MRI paramagnetic substances, e.g., chelated metal ions, e.g., of atomic numbers 21-29, 42, 44 and 58-70, inter alia, particularly gadolinium, dysprosium, iron, manganese, etc., or magnetic particles; for X-ray imaging, iodinated-benzene-based compounds, or chelated heavy metals, e.g., of atomic numbers 21-29, 42, 44 and 57-83, inter alia; for radionuclide, e.g., gamma camera imaging (or radiotherapy, also), to radioactive ions, e.g., in chelated form or bonded directly to a biomodulator, e.g., to its ring portion; suitable ions are cobalts, technetium, strontium, copper, iodine, indium, e.g., $^{123}I$ or $^{131}I$, etc.; PET (positron emission tomography) via attachment to positron emitting isotopes, such as $^{43}Sc$, $^{52}Fe$, $^{55}Co$, copper, etc. Where radioactivity is the operative modality, any of the conventional techniques for radioactivity "tagging" chemical structures can be used, e.g., as described in Crockford et al., U.S. Pat. No. 4,424,200; Rhodes, U.S. Pat. No. 4,305,922; Alvarez et al., U.S. Pat. No. 4,741,900, EP-A-0 188 256, EP-A-0 289 187, EP-A-0 023 764.

Selective localization and/or modified biodistribution of these "active" moieties by means of the of the biomodulators will produce image enhancement and/or modification by the corresponding modality, MRI, X-ray, radioimaging, PET imaging, etc. NMR Spectroscopic.

Where desired, the oligosaccharide can be conjugated to the "active" moiety using any of the plethora of conventional techniques. Generally, where a metal is involved this can be accomplished by attachment to a metal binding molecule, typically a chelating agent. The order of the binding reactions, e.g., metal binding or oligosaccharide binding initially, is not critical. For instance, an oligosaccharide can be bound by means of a substituent added to the agent on a non-critical portion. Typical such substituents include OH, COOH, $NH_2$, $CONH_2$, and many others. Linking the oligosaccharide and the chelating agent can be any of a host of conventional linkers. For thorough descriptions of useful chelating agents, linking moieties, chemical methods for effecting the couplings, etc., see, e.g., U.S. Pat. Nos. 4,352,751, 4,176,173, 4,310,507, 4,668,503, 4,986,979, 4,454,106; GB 2,109,407-A; G. E. Krejarek et al., Bioch. Biophy. Res. Comm. 77, 581 (1977); Sela et al. (U.S. Pat. Nos. 4,093,607 and 4,263,279); Schwartz (U.S. Pat. No. 4,647,671); Shen et al. (U.S. Pat. No. 4,631,190); Desphande et al. (Int. J. Rad. Appl. Instrum. [B] (England) 16, 587-597 (1988)); Quadri et al. (J. Nuc. Med. 27, p. 959 (Absr. #337)(1986)); Hoseman et al. (J. Nuc. Med. 12, 455-460 (1986)); Meares et al. (Intl. J. Cancer [Suppl.] U.S. 2, 99-102 (1988); A. R. Fritzberg et al., "Specific and Stable Labeling of Antibodies with Technetium-99m with a Diamide Dithiolate Chelating Agent," Proc. Natl. Acad. Sci. 85:4025-4029 (1988); D. A. Scheinberg et al., "Tumor Imaging with Radioactive Metal Chelates Conjugated to Monoclonal Antibodies," Science 215:1511-1513 (1982); A. R. Fritzberg, "Advances in $^{99m}$Tc-Labeling of Antibodies," Nucl. Med. 26:7-12 (1987); D. J. Hnatowich et al., "DTPA-Coupled Proteins—Procedures and Precautions," Nucl. Med. Bio. 14:563-568 (1987); D. J. Hnatowich et al., Science 220:613 (1983); Manabe et al., Biochim. Biophys. Acta 883:460 (1986).

Exemplary modified imaging agents include, e.g.,

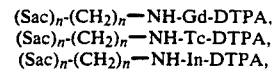

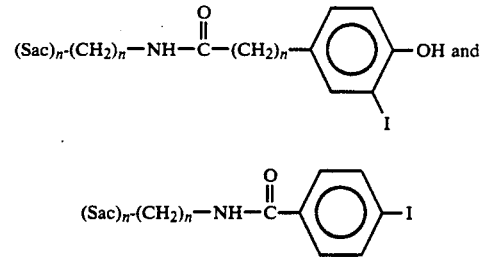

Thus, the biomodulators can be administered in accordance with this invention for the visualization of any portion (organ, tissue, etc.) of the body in which a given biomodulator is determined to concentrate, especially those suspected of being in an aberrant state in view of the general capability of biomodulators to concentrate therein, e.g., especially for the visualization of tumors, including cancerous and benign tumors such as soft tumors, such as leukemias and lymphomas, and solid tumors, such as melanomas, ovarian tumors, cervical tumors, breast tumors, lung tumors (small cell and non-small cell), colon and stomach tumors, hepatocellular tumors, pancreatic, midgut, bladder and prostate tumors, brain tumors, myelomas, and larynx tumors; senescent tissues and cells; injured tissue, especially containing endothelial cells for which biomodulators will enhance repair; defective immune cells; etc. Thus, this invention facilitates patient management by enabling the staging and evaluation of the extent of these aberrant states, such as metastasis of a tumor. PWM has also been shown to localize in areas of arthritis and in tissues affected in autoimmune disease.

By "abnormal tissue" herein is meant any tissue in a condition other than normal for a healthy host, e.g., mammals including humans, e.g., cancerous, diseased, injured, etc. Also included is senescent tissue whether due to the "normal" aging process or otherwise.

The mono- and oligosaccharide-modified imaging agents of this invention, as described above, can be administered in a manner analogous with other imaging agents in the conventional imaging and therapeutic methods, e.g., as described in Enhanced Magnetic Resonance Imaging, V. M. Runge, ed., C. V. Mosby Co. (1989) for MRI, in EP 188,256; Kozak et al., TIBTEC October 1986, 262; Radiotracers for Medical Applications, CRC Press, Boca Raton, FL., e.g., for radiodiagnostics and/or for radiotherapy, in Positron Emission Tomography of the Brain, Springer Verlag 1983, for PET, and in D. P. Swanson et al., "Pharmaceuticals in Medical Imaging," Macmillan Publishings Co., Inc., N.Y. (1990) for X-ray, in each case for imaging of various tissues described above. For example, they are typically administered prior to the performance of the imaging procedure. It is even possible for the administration to be simultaneous with the imaging where desired, e.g., in pharmacokinetic studies. The optimum time periods required for preadministration of the biomodulator to achieve localization and/or preconditioning at the target site and resultant optimum image enhancement or modification will also vary with biomodulator and/or imaging agent and/or tissue and/or imaging modality and will also be routinely determinable. Of course, imaging will occur prior to significant clearance of the biomodulator from the site, which time period can also be routinely determined by those of skill in the art. Typically, biomodulators will be administered 15 minutes to 4 hours prior to administration of the imaging agent which will be administered in a normal time period prior to performing the imaging procedure, e.g., 15 minutes to 1 hour before. The short time periods for biomodulator preadministration are derived from the advantage that they are localized rapidly at their target sites and then cleared rapidly therefrom, as discussed further below. Longer or shorter time periods are also applicable, as long as the effect of the biomodulator on the target tissue is still active when the active agent becomes bioavailable to such tissue.

The agents of this invention may be administered alone, or more typically they may be administered in combination with one of the usual physiologically acceptable excipients, e.g., water, buffers, surfactants, etc., by the usual routes, e.g., enterally, parenterally, e.g., i.v., i.m., subcutaneously. The optimum amount of the biomodulator and the imaging agent may vary with the patient, the method of imaging or therapeutic treatment employed, the location to be imaged or treated, the timing of imaging or treatment, the active agent used, etc., and is routinely determinable by one of ordinary skill in the art. Typically, the amount of biomodulator dosed for all the uses discussed herein above and below will be in the same range of the amounts thereof effective for observance of the therapeutic and other physiological effects of the biomodulators per se, e.g., their effects of normalizing cellular differentiative abnormalities, e.g., typically, 100 ng/kg-100 µg/kg. The amounts of imaging agents will be essentially the same as those amounts usually employed with such agents or with analogous agents for the given imaging modality as conventionally performed, e.g., generally doses of 0.1 mmol per kg, for gadolinium complexes, generally, doses as are well known and described, for example, in the reference material cited above.

Analogous to the use of biomodulators for "targeting" imaging moieties, the same principles can be applied to the targeting of therapeutic moieties, i.e., drugs, by conjugation of the latter to mono- or oligosaccharides via the same basic conventional procedures mentioned above. In this case, it is often preferred that the drug be attached to the biomodulator via a preferably site-specific cleavable linker as are well known in the art. See, e.g., Sela et al., U.S. Pat. No. 4,093,607, U.S. Pat. No. 4,263,279; Schwartz, U.S. Pat. No. 4,647,671; Shin et al., U.S. Pat. No. 4,631,190; Desphande et al., Intd. J. Rad. Appl. Instrum. [B](England) 16, 587–597 (1988); Quadri et al., J. Nuc. Med. 27. p. 959 (Abstract #337) (1986); Haseman et al., J. Nuc. Med. 12 455–460 (1986); Meares et al., Intl. J. Cancer [Suppl.] U.S. 2, 99–102 (1988); Hong et al., J. Med. Chem. 31, 1793 (1988).

Suitable such drugs include antitumor agents such as Ara-C, Melphalan, Methotrexate, and other folate analogs, Daunomycin, Doxorubicin, Mitomycins, Bleomycins, Mitoxantrone, Dactinomycin, etc., as well as toxins such as ricin, abrin, diptheria toxin, Pseudomonas exotoxin A, ribosomal inactivating proteins, mycotoxins, etc., but not limited thereto. Also applicable is a wide variety of other drug types, e.g., therapeutic agents in all of the major therapeutic areas including, but not limited to, anti-infectives, such as antibiotics and antiviral agents, analgesics and analgesic combinations, anthemidines, antiarthritics, antiasthmatic agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, betablockers, antiarrythmics, antihypertensives, diuretics, vasodilators including general, coronary, peripheral and cerebral, central nervous system stimulants, cough and cold preparations, decongestants, hormones, hypnotics, immunosuppressives, muscle relaxants, parasympatholytics, parasympathomimetics, psychostimulants, sedatives and tranquilizers.

By the term "interact" herein is meant any chemical or biological influence of one material on another, e.g., a bonding-type (weak or strong) relationship between two moieties, e.g., uptake of one moiety, e.g., an agent, by the other, e.g., tissue, or such as chemical attraction between a cellular oligosaccharide conformation (display) and an active agent in its vicinity or a different oligosaccharide in its vicinity, e.g., in contact therewith, such as an oligosaccharide which is part of an imaging agent of this invention.

The particular combination of biomodulator/tissue to be selected in conjunction with the modification of the biodistribution of, and thus the therapeutic effect produced by, a particular modified drug will be routinely determinable in accordance with the principles and guidance described herein, e.g., with a few routine orientation experiments. For example, where it is desired to treat abnormal tissue, for reasons explained above, essentially any biomodulator will modify such tissue and concomitantly its interaction with a therapeutic agent. As a result, the corresponding treatment of such tissue and its environment will be different from that obtainable (if at all) in the absence of the biomodulator.

The invention will be most advantageous where a biomodulator/tissue/therapeutic agent combination is employed which results in a more concentrated treatment (rather than merely an alternative treatment regimen) for the abnormal tissue than is available with the drug without biomodulator added, as will generally be the case. Thus, another advantage of this invention is that it dramatically increases the usefulness of therapeutic agents per se which are commercially available, e.g., as discussed above, thus to circumvent specific problems associated with an agent in normal use (e.g., side effects) or to further accentuate an agent's desired characteristics.

This aspect of the invention will also be particularly applicable to abnormal tissue as discussed above, e.g., cancerous (or even benign) tumors, senescent cells, injured tissue, etc.

The amounts of biomodulator to be employed will be the same as described herein for the other aspects of the use of biomodulators; the amounts of the drugs to be used will be those conventionally employable.

Formulations of the biomodulator and drug are fully conventional using the usual pharmaceutically acceptable adjuvants, e.g., as described above. Similarly, other features of the administration of the biomodulator and/or drug are as described above or otherwise fully conventional.

Of course, the underlying phenomena described herein with respect to the imaging aspects of this invention, can also be applied to NMR spectroscopic studies of oligosaccharide displays, e.g., by measuring the effects of the modified imaging agents upon interaction therewith.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

Example 1: Gd-DTPA Treatment of Tumor-Bearing Nude Rats Without Biomodulator Pretreatment Nude rats were injected with canine glioma tumor cells 7 days prior to imaging over the tumor regions with NMR. Regression analysis of the data in FIG. 1 indicates that the image intensity declines logarithmically over time, indicating standard wash-out kinetics and no specific interaction of the Gd-DTPA with tumor tissue.

Example 2: Gal-Gd-DTPA Treatment of Tumor-Bearing Nude Rats With Biomodulator Pretreatment FIG. 2 shows the results of a similar experiment as in Example 1, except that the tumor-bearing rat was treated with pokeweed mitogen biomodulator for 10 days prior to imaging and the imaging agent was galactosamine-modified DTPA, Gal-Gad-DTPA. In contrast to non-biomodulator-pretreated animals to which Gal-Gd-DTPA was administered as an imaging agent, which showed standard wash-out kinetics such as shown in FIG. 1, the wash-out kinetics of the biomodulator-pretreated rat were linear (FIG. 2), indicating that there was a biomodulator-dependent enhancement of interaction of a specific agent to the tumor tissue.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of enhancing the image of tissue obtainable by a particular imaging modality comprising administering a biomodulator and an imaging agent for said modality, said biomodulator and said agent and the amounts thereof being effective for enhancement or other modification of the image of said tissue, and said agent comprising:

a first portion per se effective to affect the image achievable by said modality; and a second, mono- or oligosaccharide portion effective to interact with cellular oligosaccharide displays.

2. A method of claim 1, wherein said first portion corresponds to a non-tissue-specific imaging agent.

3. A method of claim 1, wherein said first portion corresponds to a tissue-specific imaging agent.

4. A method of claim 2, wherein said tissue is abnormal tissue.

5. A method of claim 3, wherein said tissue is abnormal tissue.

6. A method of claim 4, wherein said second portion is a mono- or disaccharide.

7. A method of claim 5, wherein said second portion is a mono- or disaccharide.

8. A method of claim 4 for radionuclide imaging of abnormal tissue of a host.

9. A method of claim 5 for radionuclide imaging of abnormal tissue of a host.

10. A method of claim 4 for magnetic resonance imaging of abnormal tissue of a host.

11. A method of claim 5 for magnetic resonance imaging of abnormal tissue of a host.

12. A method of claim 4 for X-ray or positron emission tomography imaging of abnormal tissue of a host.

13. A method of claim 5 for X-ray or positron emission tomography imaging of abnormal tissue of a host.

14. A method of claim 4, wherein the amount of said biomodulator is 100 ng/kg–100 µg/kg.

15. A method of claim 5, wherein the amount of said biomodulator is 100 ng/kg–100 µg/kg.

16. A method of claim 4 for visualizing a tumor.

17. A method of claim 5 for visualizing a tumor.

18. A method of claim 8, wherein said first portion radioactively tagged human serum albumin or radioactively tagged bovine serum albumin.

19. A method of claim 11, wherein said agent is Gd-DTPA-galactose.

20. A method of claim 4, wherein the biomodulator is (a) a compound of formula (I)

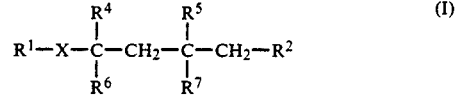

wherein $R^1$ is an optionally substituted aromatic, cycloaliphatic or heterocyclic ring system, $R^2$ is —CH$_2$OH, —CHO, —COOR$^3$, —COSR$^3$, —CONR$^8$R$^9$ or the corresponding lactone

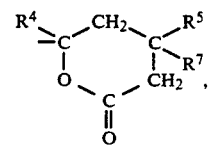

wherein $R^3$ is H or C$_{1-10}$-alkyl, $R^4$ and $R^5$ are each independently H or C$_{1-6}$-alkyl, $R^6$ and $R^7$ are each independently OR, NHR or SR wherein R is H or C$_{1-4}$-alkanoyl, $R^8$ and $R^9$ are each independently H or $C_{1-10}$-alkyl, and X is $C_{2-3}$-alkylene, $C_{2-3}$-alkenylene, $C_{2-3}$-alkynylene, a cyclopropylene group, $-OCH_2-$ or $-SCH_2-$;

(b) a compound of formula (II) (swainsonine)

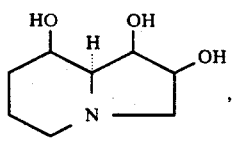

or an indolizidine alkaloid having an electronically similar 1,3-diol structure;

(c) cellular activator and differentiator (CAD); and (d) pokeweed mitogen; and having the biological activity of a biomodulator.

21. A method of claim 5, wherein the biomodulator is (a) a compound of formula (I)

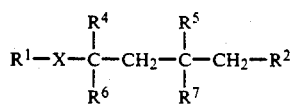

wherein $R^1$ is an optionally substituted aromatic, cycloaliphatic or heterocyclic ring system, $R^2$ is $-CH_2OH$, $-CHO$, $-COOR^3$, $-COSR^3$, $-CONR^8R^9$ or the corresponding lactone

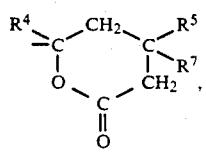

wherein $R^3$ is H or $C_{1-10}$-alkyl, $R^4$ and $R^5$ are each independently H or $C_{1-6}$-alkyl, $R^6$ and $R^7$ are each independently OR, NHR or SR wherein R is H or $C_{1-4}$-alkanoyl, $R^8$ and $R^9$ are each independently H or $C_{1-10}$-alkyl, and X is $C_{2-3}$-alkylene, $C_{2-3}$-alkenylene, $C_{2-3}$-alkynylene, a cyclopropylene group, $-OCH_2-$ or $-SCH_2-$;

(b) a compound of formula (II) (swainsonine)

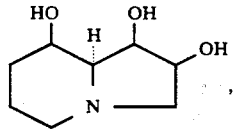

or an indolizidine alkaloid having an electronically similar 1,3-diol structure;

(c) cellular activator and differentiator (CAD); and (d) pokeweed mitogen; and
having the biological activity of a biomodulator.

22. A method of claim 1, wherein said imaging agent is

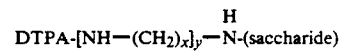

whereby 1 or 2 carboxyl groups on DTPA are amidated by a saccharide which is an α- or β-D-galactosamine, D-glucosamine, D-mannosamine, α- or β-D-lactosamine, α- or β-D-galactoxylamine, D-glucosylamine, D-mannosylamine, α- or β-D-lactosylamine, and y is 0; or, whereby one or two carboxyl groups on DTPA are amidated by an N-alkyl-saccharide as defined above, wherein -x is 1–10; and y is 1.

23. A method of claim 1, wherein said imaging agent is

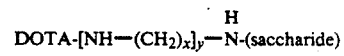

whereby a carboxyl group on DOTA is amidated by a saccharide which is an α- or β-D-galactosamine, D-glucosamine, D-mannosamine, α- or β-D-lactosamine, α- or β-D-galactoxylamine, D-glucosylamine, D-mannosylamine, α- or β-D-lactosylamine, and y is 0; or, whereby a carboxyl group on DOTA is amidated by an N-alkyl-saccharide as defined above, wherein x is 1–10; and y is 1.

24. A method of claim 1, wherein said imaging agent is

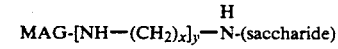

whereby a carboxyl group on MAG is amidated by a saccharide which is an α- or β-D-galactosamine, D-glucosamine, D-mannosamine, α- or β-D-lactosamine, α- or β-D-galactoxylamine, D-glucosylamine, D-mannosylamine, α- or β-D-lactosylamine, and y is 0; or, whereby a carboxyl group on MAG is amidated by an N-alkyl-saccharide as defined above, wherein x is 1–10; and y is 1.

25. A method of claim 20, wherein the biomodulator is

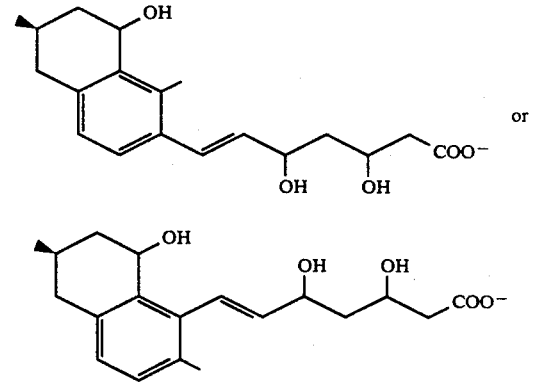

having a 3S,5R; 3R,5R; or 3S,5S stereoconfiguration.

* * * * *